US008834839B2

(12) United States Patent
Schaffer et al.

(10) Patent No.: US 8,834,839 B2
(45) Date of Patent: Sep. 16, 2014

(54) LABELED MOLECULAR IMAGING AGENTS, METHODS OF MAKING AND METHODS OF USE

(75) Inventors: Paul Schaffer, Richmond (CA); Brian Duh-Lan Lee, Rexford, NY (US); Kande Kankanamalage Dayarathna Amarasinghe, Ellicott City, MD (US); Faisal Ahmed Syud, Clifton Park, NY (US); Rong Zhang, Niskayuna, NY (US); Jack Mathew Webster, Niskayuna, NY (US); Jennifer Lynne Huntington, Saratoga Springs, NY (US)

(73) Assignee: General Electric Company, Schenectady, NY (US)

(*) Notice: Subject to any disclaimer, the term of this patent is extended or adjusted under 35 U.S.C. 154(b) by 915 days.

(21) Appl. No.: 12/430,573

(22) Filed: Apr. 27, 2009

(65) Prior Publication Data
US 2010/0272641 A1 Oct. 28, 2010

(51) Int. Cl.
A61K 51/04 (2006.01)
C07C 323/59 (2006.01)
C07B 59/00 (2006.01)
A61K 49/00 (2006.01)
C07C 323/58 (2006.01)
C07F 5/02 (2006.01)

(52) U.S. Cl.
CPC .......... A61K 51/0406 (2013.01); C07C 323/59 (2013.01); C07B 59/001 (2013.01); A61K 49/0052 (2013.01); A61K 49/0019 (2013.01); C07B 2200/05 (2013.01); C07C 323/58 (2013.01); C07F 5/022 (2013.01)
USPC ...................................................... 424/1.65

(58) Field of Classification Search
None
See application file for complete search history.

(56) References Cited

U.S. PATENT DOCUMENTS 5,171,563 A 12/1992 Abrams et al.
6,953,567 B2 10/2005 Griffith
7,211,240 B2 5/2007 Arbogast et al.

FOREIGN PATENT DOCUMENTS

WO 2006/096207 A2 9/2006

OTHER PUBLICATIONS

Liu Y, Li XY, Guo DS, Chi H. Synthesis of L-cystine modified cyclodextrin monomers and dimers with primary-side versus secondary-side and their molecular binding behaviors. 2008 Supramol. Chem. 20: 609-617.*
Sugden JK. Photochemistry of dyes and fluorochromes used in biology and medicine: some physicochemical background and current applications. 2004 Biotech. Histochem. 79: 71-90.*
Massoud TF, Gambhir SS. Molecular imaging in living subjects: seeing fundamental biological processes in a new light. 2003 Genes Dev. 17: 545-580.*
Lee SH, Moon JJ, Miller JS, West JL. Poly(ethylene glycol) hydrogels conjugated with a collagenase-sensitive fluorogenic substrate to visualize collagenase activity during three-dimensional cell migration. 2007 Biomaterials 28: 3163-3170.*
Mohs AM, Wang X, Goodrich KC, Zong Y, Parker DL, Lu ZR. PEG-g-poly(GdDTPA-co-L-cystine): a biodegradable macromolecular blood pool contrast agent for MR imaging. 2004 Bioconjug. Chem. 15: 1424-1430.*
A. Banjac et al., "The cystine/cysteine cycle: a redox cycle regulating susceptibility versus resistance to cell death," National Publishing Group, Oncogene, vol. 27, 2008, pp. 1618-1628.
Maria Teresa Bassi et al., "Identification and characterisation of human xCT that co-expresses, with 4F2 heavy chain, the amino acid transport activity system xc-," Pflugers Arch—European Journal Physical, vol. 442, 2001, pp. 286-296.
Z. Dai et al., "Chemoinformatics Analysis Identifies Cytotoxic Compounds Susceptible to Chemoresistance Medicated by Glutathione and Cystine/Glutamate Transport System Xc-," Journal Medicinal Chemistry, vol. 50, No. 8, 2007, pp. 1896-1906.
PW Gout et al., Sulfasalazine, a potent suppressor of lymphoma growth by inhibition of the Xc cystine transporter: a new action for an old drug, National Publishing Group, 2001, vol. 15, pp. 1633-1640.
Y. Huang et al., "Cystine-Glutamate Transporter SLC7A11 in Cancer Chemosensitivity and Chemoresistance," Research Article, Cancer Research, vol. 65, No. 16, Aug. 15, 2005, pp. 7446-7454.
J.Y. Kim et al., "Human cystine/glutamate transporter: cDNA cloning and upregulation by oxidative stress in glioma cells," Elsevier, Biochimica et Biophysica Acta, vol. 1512, 2001, pp. 335-344.
R. L. Lackman et al., "Innate Immune Recognition Triggers Secretion of Lysosomal Enzymes by Macrophages," Traffic, vol. 8, 2007, pp. 1179-1189.
M. Lo et al., "The Xc cystine/glutamate antiporter: a mediator of pancreatic cancer growth with a role in drug resistance," British Journal of Cancer, vol. 99, 2008, pp. 464-472.
K. Mawatari et al., "Reactive Oxygen Species Involved in the Glutamate Toxicity of C6 Glioma Cells Via XC Antiporter System," Pergamon, Neuroscience, vol. 73, No. 1, 1996, pp. 201-208.
S. A. Patel et al., Differentiation of substrate and non-substrate inhibitors of transport system Xc: an obligate exchanger of L-glutamate and L-cystine, Elsevier, Neuro Pharmacology, vol. 46, 2004, pp. 273-284.
C. Plathow et al., "Tumor Cell Metabolism Imaging," The Journal of Nuclear Medicine, vol. 49, No. 6, Jun. 2008, pp. 43S-63S.
H. Sato et al., "Induction of cystine transport activity in mouse peritoneal macrophages by bacterial lipopolysaccharide," Biochem. Journal, vol. 310, 1995, pp. 547-551.
H. Sato et al., "Induction of cystine transport via system Xc and maintenance of intracellular glutathione levels in pancreatic acinar and islet cell lines," Elsevier, Biochimica et biophysica Acta, vol. 1414, 1998, pp. 85-94.

(Continued)

Primary Examiner — Michael G Hartley
Assistant Examiner — Jennifer Lamberski

(57) ABSTRACT

Imaging agents that comprise labeled substrates of the cystine/glutamate antiporter of cells, whereby the methods of use comprise introducing the labeled agents into cells via the cystine/glutamate antiporter, which are then reduced to a labeled cysteine, and subsequently detected in the cell.

5 Claims, 12 Drawing Sheets

(56) References Cited

OTHER PUBLICATIONS

H. Sato et al., "Cloning and Expression of a Plasma Membrane Cystine/Glutamate Exchange Transporter Composed of Two Distinct Proteins," The Journal of Biological Chemistry, vol. 274, No. 17, Apr. 23, 1999, pp. 11455-11458.

K. Taguchi et al., Induction of cystine/glutamate transporter in bacterial lipopolysaccharide induced endotoxemia in mice, Journal of Inflammation, BioMed Central, vol. 4, No. 20, Sep. 2007.

L. Varagnolo et al., "F-labeled Radiooharmaceuticals for PET in Oncology, Excluding FDG," Nuclear Medicine & Biology, 2000, vol. 27, pp. 103-112.

G. Wu et al., "Glutathione Metabolism and Its Implications for Health," The Journal of Nutrition, 2004, downloaded from jn.nutrition.org, Mar. 9, 2010.

R. C. Mease et al., N-[N-[{(S)-1,3-Dicarboxypropyl]Carbamoyl]-4-[18F]Fluorobenzyl-L-Cysteine,[18]DCFBC: A New Probe for Prostate Cancer, Imaging, Diagnosis, Prognosis, Clinical Cancer Research, vol. 14, No. 10, May 15, 2008, pp. 3036-3043.

B. de Bruin et al., "1-[3-(2[18F]Fluoropyridin-3-ylogxy)propyl]pyrrole-2,5-dione: Design, Synthesis, and Radiosynthesis of a New [18F]Fluoropyridine-Based Maleimide Reagent for the Labeling of Peptides and Proteins," Bioconjugate Chemical, vol. 16, 2005, pp. 406-420.

M. Berndt et al., "Labeling of low-density lipoproteins using the 18F-labeled thiol-reactive reagent N-[6-(4-[18F]fluorobenzylidene)aminooxyhexyl]maleimide," Elsevier, Science Direct, Nuclear Medicine and Biology, vol. 34, 2007, pp. 5-15.

T. Poethko et al., "Chemoselective pre-conjugate radiohalogenation of unprotected mono- and multimeric peptides via oxime formation," Radiochim. Acta, vol. 92, 2004, pp. 317-327.

* cited by examiner

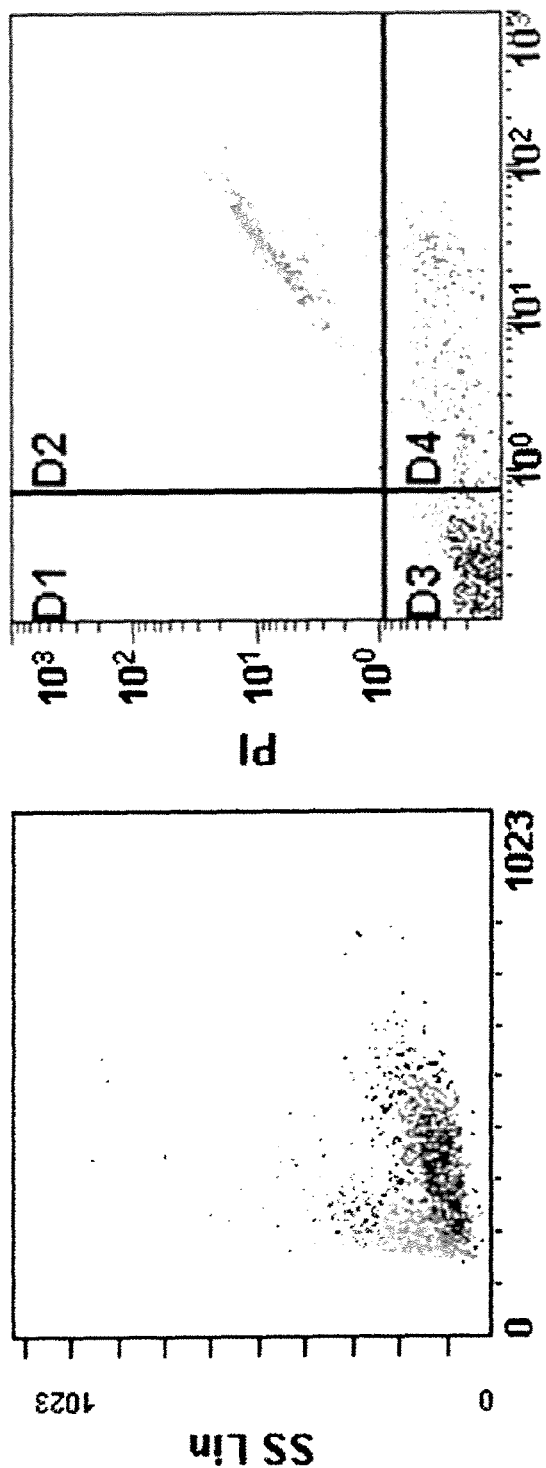

| | DBC | DBC (650 | DB Cystathionione | MBC | Neg control |
|---|---|---|---|---|---|
| Fold Intensity Shift | 7.2 | 2.8 | 4.6 | 26.6 | N/A |

60 minutes

LABELED MOLECULAR IMAGING AGENTS, METHODS OF MAKING AND METHODS OF USE

BACKGROUND

The invention relates generally to labeled molecular imaging agents and more particularly to imaging agents that are taken up by the cells via the cystine/glutamate transporter.

The concept of molecular imaging promises specific contrast enhancement of molecular signatures of pathology and requires targetable biomarkers that are specifically regulated in certain pathological indications. While such a specific molecular contrast agent could have great utility for imaging and diagnosing disease; validation of a truly specific biomarker has proven to be very difficult. Even if an agent to such a specific biomarker is created, the market for such an agent will be limited to the prevalence of this indication. Therefore there is great interest in developing molecular contrast agents that can be utilized to image a variety of pathological indications. Most imaging agents target specific tissue or cell types, or specific therapies, or they degrade rapidly over time. One example of an agent that is directed at broader applications is 18-F-fluorodeoxyglucose (FDG) that makes use of the glucose transporter. $^{18}$F-FDG is preferentially taken up by cells that have an increased requirement for glucose, and then is trapped inside the cell. FDG can be used clinically for the diagnosis, staging and monitoring of many cancers as well as monitoring metabolism in the heart and brain. $^{18}$F-FDG is not a substrate for sodium-dependent glucose transporters found in the kidney tubules, which prevents its renal resorption and enhances clearance In vivo oxidative stress is recognized as an indicator of cellular stress. Efforts to image this stress have involved imaging animals using electron paramagnetic resonance (EPR). EPR is a technique for detecting unpaired electrons as would occur with the creation of free radicals in oxidative stress. Essentially an agent is used which is considered to be an EPR probe which is sensitive to organ antioxidative activity as a measure of oxidative stress.

Others have also looked at using a 13-C-glycine chemical shift MRI to detect glycine uptake and conversion to glutathione in an animal model of chemotherapy treatment of tumors in vivo. Still others, having developed imaging agents to detect apoptotic cells in vivo for monitoring chemotherapy treatment (e.g. labelled Annexin V which is a rather large protein. Aposense by Neurosurvival Technologies which is a family of small molecules which is reported to enter specifically into only apoptotic cells.

BRIEF DESCRIPTION

The imaging agents and methods of the invention take advantage of the cellular amino acid transporter (cystine/glutamate antiporter, Xc~), which is activated under conditions of cellular oxidative stress. These labeled molecular imaging agents and methods of the invention provide several benefits, including but not limited to, their use in a wide variety of diagnostic and therapeutic monitoring applications; they are small molecules and comprise labeled variants of a natural compound found in the body, and would be administered at tracer levels with physiological concentrations well below those that generate toxic response, therefore toxicity/immune response is expected to be low; and because the imaging agents act as a transporter substrate, the agents benefit from amplification of the signal because the molecular imaging agent is trapped once inside the cell, unlike other molecular binders in which the imaging agent's signal is limited to the stoichiometric binding of a cell surface epitope. The labeled substrates of the invention for the cystine/glutamate transporter may also be used to introduce compounds in a target for therapeutic purposes.

As a labeled substrate of the cystine/glutamate transporter, these imaging agents may be used for any disease or condition that relates to increased oxidative stress. For example, the imaging agents may be used image apoptotic cells in vivo. Such noninvasive monitoring of apoptotic cell death is useful, for example without limitation, to monitor chemotherapy effectiveness, tissue damage due to ischemia/stroke, traumatic injury, and transplant rejection. Imaging of oxidative stress is also useful for diagnosing and monitoring inflammatory diseases or any pathological indication that includes oxidative stress or tissue damage.

Additionally, upregulation of the cystine/glutamate transporter is also associated with chemotherapy resistance in some tumors. Therefore, non-invasive imaging of tumors with basal high cystine uptake could result in identification of tumors likely to be resistant to certain therapies; which could result in efficacious changes in treatment regimens.

An embodiment of the imaging agent of the invention, generally comprises a compound having the structure I,

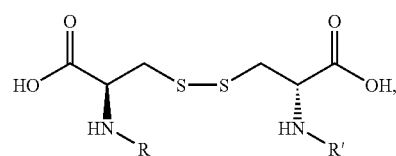

wherein only one of the Rs comprises a fluorescent or radioisotopic label. In some embodiments, the cystine compound has structure II:

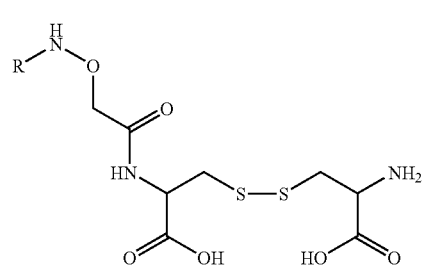

wherein R comprises a radioisotopic label. In some embodiments, the cystine compound has the more specific structure III:

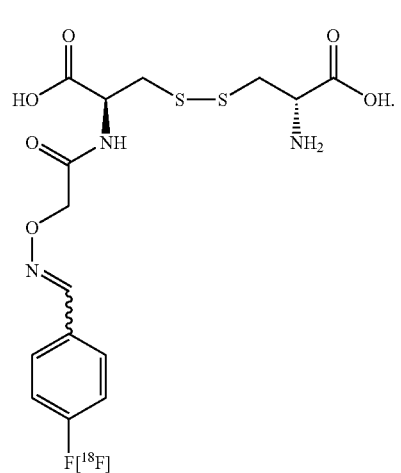

In some other embodiments, the cystine compound has structure IV:

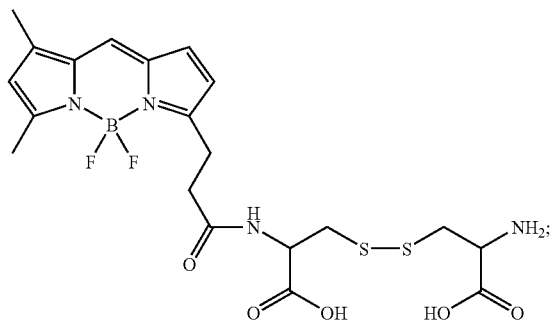

IV wherein structure IV comprises a fluorescent label.

An example of the method of the invention, for detecting oxidative stress in cells generally comprises: introducing an imaging agent comprising a labeled cystine into a cystine/glutamate antiporter of the cells; allowing the intracellular labeled cystine to be reduced into a labeled cysteine; detecting the labeled cysteine in the cell. For example, for some applications, the labeled cystine may be detected in apoptotic cells.

In some non-limiting examples of the method, the labeled cystine used in the method may have the structure I,

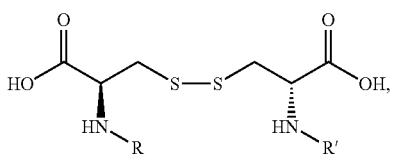

I wherein only one of the Rs comprises a fluorescent or radioisotopic label. In some more specific, non-limiting examples of the method, the labeled cystine has structure IV:

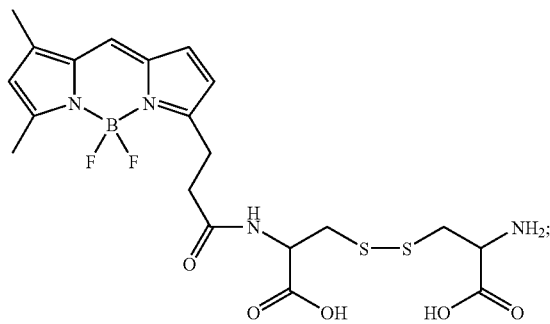

IV wherein structure IV comprises a fluorescent label. In other more specific, non-limiting examples of the method, the labeled cystine has structure II:

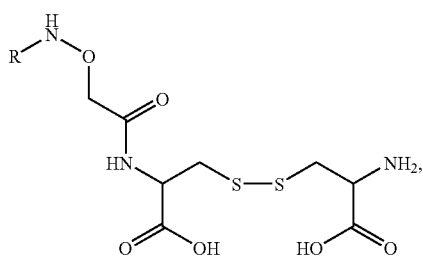

II wherein structure II comprises a radioisotopic label. In a more specific, non-limiting example, the labeled cystine has structure III:

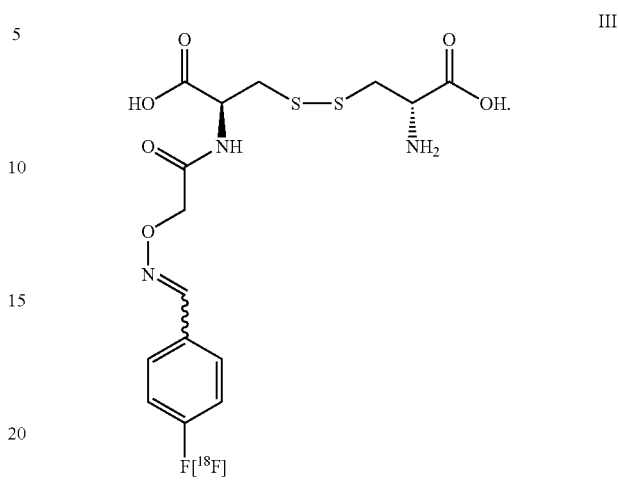

III

Another embodiment of the imaging agent of the invention generally comprises, a labeled small molecule substrate of a cystine/glutamate transporter (xc-), such as, but not limited to, Structures I, II, III, IV, V and VI.

A non-limiting example of a method for imaging, generally comprises: using a cystine compound having the Structure I:

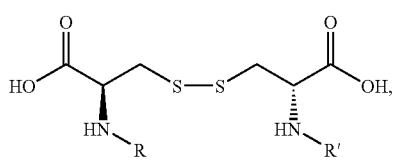

I wherein only one of the Rs comprises a fluorescent or radioisotopic label; and wherein the compound is detected using one or more of, fluorescence microscopy, laser-confocal microscopy, cross-polarization microscopy, nuclear scintigraphy, positron emission tomography, single photon emission computed tomography, magnetic resonance imaging, magnetic resonance spectroscopy, computed tomography, or a combination thereof.

A example of the method for imaging a biological target having a cystine/glutamate transporter, generally comprises, introducing into the target an imaging agent comprising a labeled small molecule substrate via the cystine/glutamate transporter; and detecting the imaging agent using one or more of, fluorescence microscopy, laser-confocal microscopy, cross-polarization microscopy, nuclear scintigraphy, positron emission tomography, single photon emission. In addition, if the small molecule substrate is labeled with a magnetic label, the methods may also be used in connection with computed tomography, magnetic resonance imaging, magnetic resonance spectroscopy, computed tomography, or a combination thereof.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein:

FIG. 2A is a forward scatter/side scatter plot showing some late apoptotic Jurkat cells (light gray) with a different granularity than non-apoptotic Jurkat cells (darker gray). FIG. 2B is a multi-quadrant scatter plot showing Annexin V and propidium iodide (PI) negative cells in quadrant D3 and represent non-apoptotic cells; showing Annex in V-Cy5 positive and propidium iodide (PI) negative cells in Quandrant D4 representing early apoptotic cells; and showing Annexin V positive, cells in Quandrant D2 representing late apoptotic and necrotic cells FIG. 3A is a graph showing untreated cells demonstrating some uptake or nonspecific binding of the DBC molecule. FIG. 3B is a graph showing that staurosporine induced cells have three subpopulations of cells, low intensity DBC fluorescence representing normal cells, intermediate intensity representing early apoptotic cells and high intensity representing late apoptotic cells. FIG. 3C is a graph showing that staurosporine induced cells that are exposed to the cystine/glutamate transporter inhibitor sulfasalazine (sasz) have a different result; a population of cells with intermediate DBC staining represents late apoptotic cells, while Early apoptotic cells are in the low DBC intensity population. FIG. 4D is a bar chart showing the percentage of cells labeled greater than baseline DBC staining for normal, early apoptotic and late apoptotic cells (as determined by Annexin V and PI staining).

FIG. 5 A-C shows results from flow cytometric analysis of MonoBodipyCystine (MBC) uptake in Jurkat cells with Staurosporine (STN) to induce oxidative stress/apoptosis with and without sulfasalazine (sasz) to inhibit the cystine/glutamate transporter.

DETAILED DESCRIPTION

Figure 1:
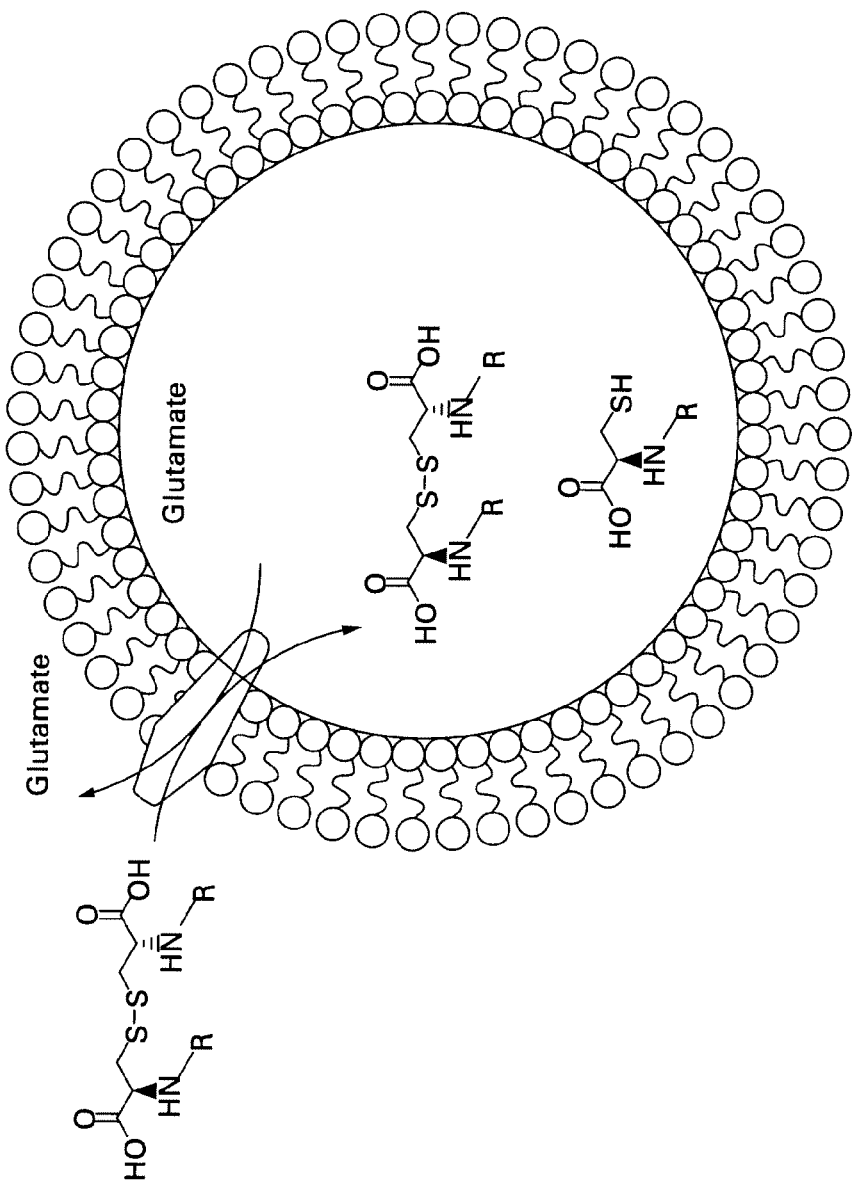
FIG. 1 is a flow diagram of an embodiment of the imaging agent of the invention being transported into a cell via the cystine/glutamate antiporter.

To more clearly and concisely describe and point out the subject matter of the claimed invention, the following definitions are provided for specific terms, which are used in the following description and the appended claims.

As used herein, the term "cystine/glutamate transporter" are used interchangeably with, and include, the terms cystine/glutamate antiporter, cystine/glutamate exchanger, cystine transporter, xc(-), Xc(-), system xc(-), and amino acid transport system Xc(-). The transport system comprises dimer of two proteins and includes, but is not limited to: protein xCT and protein CD98 (4F2hc, heavy chain of the 4F2 surface antigen, SLC3A2); protein xCT which is the subunit specific to the xc(-) system; protein CD98 which is a subunit common to a number of transporters with different substrates; and protein xCT that may also dimerize with rBAT, another subunit common to multiple transporters.

As used herein, the term "fluorescent label" includes, but is not limited to, fluorescent imaging agents and fluorophores, that are chemical compounds, which when excited by exposure to a particular wavelength of light, emit light at a different wavelength. Fluorophores may be described in terms of their emission profile, or color, and are the component of a molecule that causes the molecule to be fluorescent. It is typically a functional group that absorbs energy of a specific wavelength or range of wavelengths and re-emit energy at different but equally specific wavelengths or ranges.

As used herein, the term "radioisotopic label" includes, but is not limited to, radioisotopes that are used in a compound to trace or visualize the compound, or the mechanism of a chemical reaction, in a chemical or biological process, or biological substances, organisms and systems. Such labels are useful, for example, in connection with imaging and detection systems. Examples of suitable radioisotopic labels include, but are not limited to, $^{123}$—I, $^{125}$—I, $^{131}$—I, $^{18}$—F, $^{11}$C, $^{62}$Cu, $^{64}$Cu, $^{67}$Cu, $^{67}$Ga and $^{68}$Ga.

The cystine/glutamate transporter is not typically expressed or has extremely low expression in most tissues, but is upregulated in cells exposed to oxidative stress. Cystine, which comprises two disulfide-linked cysteine amino acids, is a natural substrate for this transporter. The cystine/glutamate antiporter (xc- system) is an amino acid transporter (designated SLC7A11) made up of two protein subunits; 4F2hc/CD98, a common subunit for a few classes of transport systems, and xCT, which is specific to the cystine/glutamate exchanger. The effect of upregulation of the transporter is an increase in cystine uptake; which is then reduced to cysteine inside the cell. Intracellular cysteine is the rate limiting substrate for glutathione synthesis. Glutathione is the cells primary anti-oxidant to defend against oxidative stress. Intracellular cysteine is incorporated into one of two pathways, glutathione synthesis or protein synthesis.

Generally, the imaging agents of the invention comprise labeled cystine and any analogs of cystine that maintain the attributes necessary to be a substrate of the cystine/glutamate antiporter. As shown in FIG. 1, the imaging agents serve as a substrate for the cystine/glutamate antiporter. Cystine labeled at a free amine is a substrate for the xc- transporter. After transport into the cell, R-cystine is reduced to an R-cysteine and an unlabeled cysteine. R-cysteine is not metabolized and cannot exit via the transporter. Therefore it is retained in a cell that is responding to oxidative stress.

The imaging agents may be detected by its emitted signal, such as autofluorescence emission or optical properties of the agent. The method of detection of the compounds may include, but are not necessarily limited to, fluorescence microscopy, laser-confocal microscopy, cross-polarization microscopy, nuclear scintigraphy, positron emission tomography ("PET"), single photon emission computed tomography ("SPECT"), or a combination thereof, depending on the intended use and the imaging methodology available to the medical or research personnel.

The labeled substrates of the invention for the cystine/glutamate transporter may also be used to introduce labeled compounds, such as, but not limited to, a cystine substrate labeled with $^{131}$I, into a target for therapeutic purposes.

Some embodiments of the imaging agents generally have Structure I,

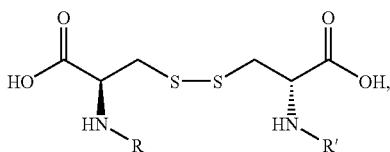

I wherein only one of the Rs comprises a fluorescent or radioisotopic label.

The disulfide bond of Structure I is reduced inside the cell and will no longer be a substrate for the xc- transporter so that the agent cannot leave the cell via this route. A fluorescent or radioisotope label (R) will be conjugated to an amine, so that the resulting reduced intracellular agent will not be metabolized. The resulting agent therefore enters and is retained in the cells with an activated xc- transporter. A single-labeled cystine has an H at the R' position, but an additional label may also be appended to the second amine at the R' position.

Using labeled cystine as an example, cystine is labeled at one or two of the free amines. When imported into the cell via the transporter, it will be reduced to labeled cysteine, which is no longer a substrate of the transporter and therefore could not be expelled from the cell by the same mechanism of entry. Because the amine is conjugated to the label, the labeled cysteine will not be a substrate for glutathione synthesis or protein synthesis and the label will be trapped in the cells.

In a wide variety of human tissues and cells examined, the xc- transporter is predominantly expressed brain, but also in pancreas and in cultured cell lines. The xc- transporter expression is very low in most tissues, but can be upregulated under conditions of oxidative stress and when cells are grown in culture. The xc- transporter is induced under a number of conditions, including apoptotic stimuli, oxidative stress, inflammation, cystine deprivation and chemotherapy resistance. For example, radioisotope labels such as $^{18}$—F, $^{68}$Ga, $^{62}$Cu and $^{64}$Cu, may be used for in vivo PET imaging, as well as in vitro detection of cellular oxidative stress.

One or more of the imaging agents of the invention comprises labeled cystine molecules that comprise fluorescent dyes and prothstetic groups to enable radioisotope labeling where labeling occurs at the amine groups of the cystine. Non-limiting examples include: green fluorescent cystine molecules such as DiBodipy(FL)-Cystine and MonoBodipy (FL)-Cystine; red fluorescent cystine molecules such as DiBodipy(650)-Cystine and MonoBodipy(650)-Cystine; and aminoxy(AO) derivatives of cystine that are labeled with 18F-flurobenzaldehyde or 19-F-fluorobenzaldehyde, including DiAO-Cystine and MonoAO-Cystine; each of which is labeled with 18F-fluorobenzaldehyde or 19F-fluorobenzaldehyde.

Following are non-limiting examples used to illustrate various embodiments of the imaging agents and methods of use.

EXAMPLE 1

Human Jurkat cells were cultured with or without 1 uM staurosporine for 16 hours in an in vitro assay for apoptotic cells and stained with propidium iodide(PI) and Cy5-Annexin V (Annexin). Typically ~30-50% of cells were found to be in some stage of apoptosis or necrosis. Flow cytometry was used to identify population of cells defined as normal (PI and Annexin negative), early apoptotic (PI negative, Annexin positive), and late apoptosis and necrosis (PI and Annexin positive). The results are shown in FIGS. 2A and 2B. FIG. 2A is a forward scatter/side scatter plot showing some late apoptotic cells (light gray) with a different granularity than non-apoptotic cells (darker gray). In FIG. 2B, Annexin V and PI negative cells are shown in quadrant D3 and represent non-apoptotic cells. Cells in quadrant D4 indicate early apoptotic cells that are positive for Annexin V staining, but negative for PI staining. Cells in quadrant D2 indicate late apoptotic and necrotic cells that are positive with both Annexin V and PI staining.

EXAMPLE 2

Jurkat cells were incubated with (FIG. 3B) and without (FIG. 3A) 1 μM staurosprine (STN) for 16-18 hours, stained with Annexin V-Cy5 and propidium iodide, and incubated with DBC for 30 minutes. DBC is a commercially available product from Invitrogen (catalog #B20340), which is sold for the purpose of reversible thiol labeling of nucleotides, proteins and cells via a disulfide exchange reaction at acidic conditions. DBC has the structure shown below.

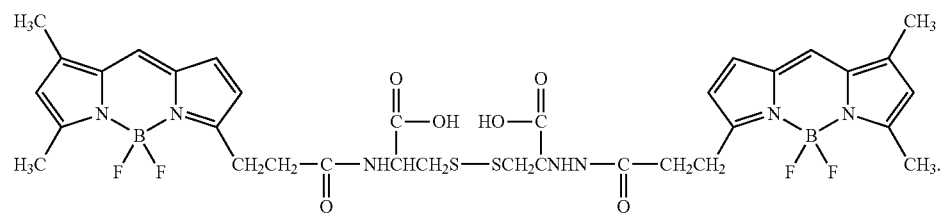

Figure 3A:
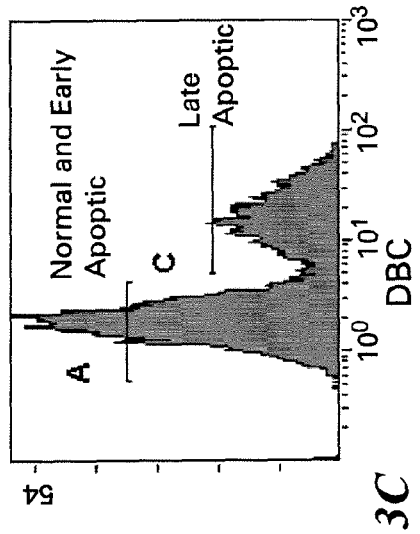
FIG. 3A-D shows results from flow cytometric analysis of DBC uptake in Jurkat cells with and without staurosporine (STN) to induce oxidative stress/apoptosis and with and without sulfasalazine (sasz) to inhibit the cystine/glutamate transporter.
Figure 3B:
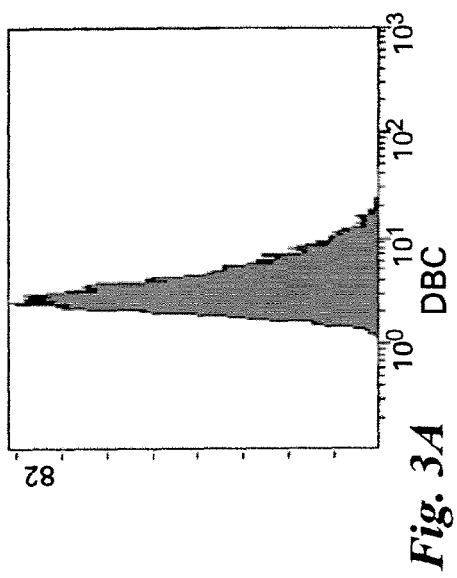
Figure 3C:
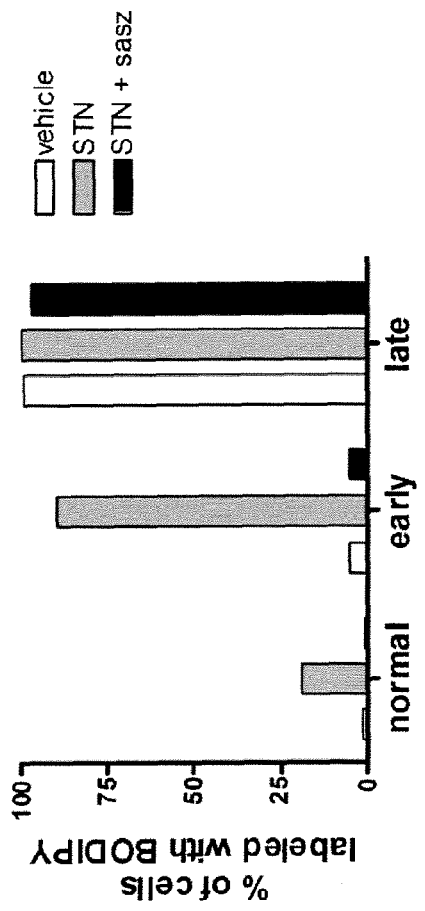
Figure 3D:
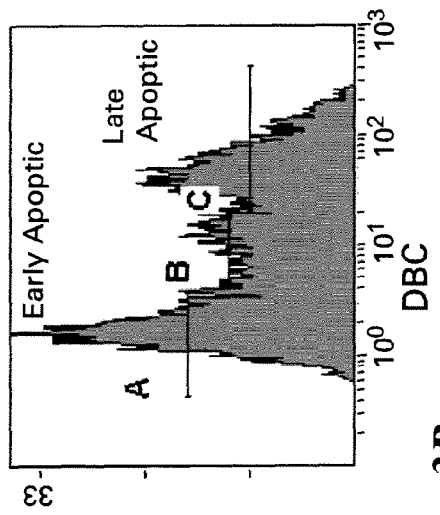

In FIG. 3A, untreated cells show some low intensity fluorescence corresponding to uptake or nonspecific binding of the DBC molecule. In FIG. 3B, staurosporine induced cells have a subpopulation of cells with high intensity DBC staining and this correlated primarily to the late apoptotic/necrotic cells (+Annexin V, +PI). A population of cells with intermediate DBC staining also appeared, which correlates well with the early apoptotic cells (+Annexin V, −PI). To more specifically address the role of the the xc- transporter in this apoptotic cell labeling assay, Jurkat cells were also incubated with sulfasalazine, a potent specific inhibitor of the xc- transporter. Cells were treated as in FIG. 2B except that a specific inhibitor of the cystine/glutamate transporter (sulfasalazine, sasz) was added at the same time as the: DBC (FIG. 3C). In FIG. 3C, a population of cells with intermediate DBC staining was found, which correlated well only with late apoptotic cells (+Annexin V, +PI). In FIG. 3D, cells were categorized as normal, early apoptotic, or late apoptotic as in Example 1, and the percentage of cells with increased DBC staining was recorded for each category. Early and late apoptotic cells were labeled with DBC, but this was only inhibited by sasz in the early apoptotic cells. As such DBC does label early apoptotic cells via activity of the cystine-glutamate transporter and acts as a transporter substrate even though it is conjugated to two fluorophores via the amines of cystine. This data shows that the uptake seen in early apoptotic cells with DBC is dependent upon the xc- transporter, rather than some other mechanism.

EXAMPLE 3

Figure 4A:
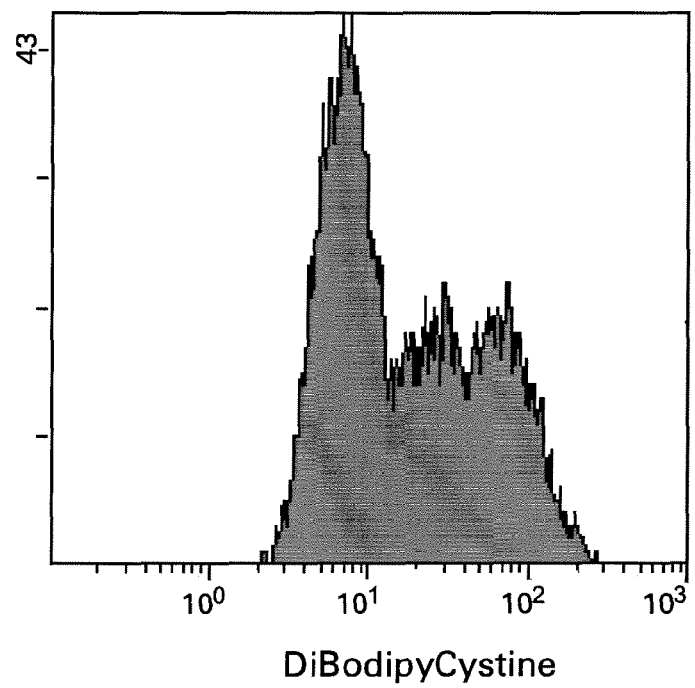
FIGS. 4A shows uptake of DBC in Jurkat cells treated with STN for 18 hours.
Figure 4B:
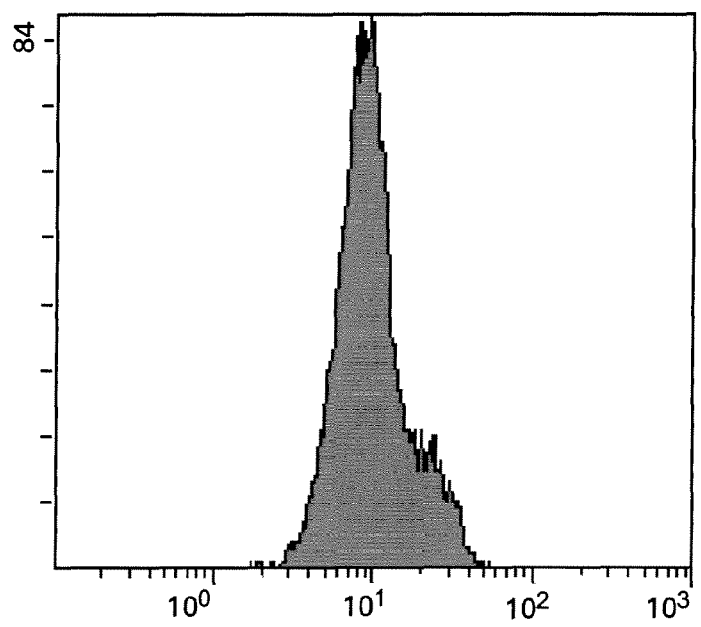
FIG. 4B shows a comparison of the same cells incubated with DiBodipy(650) Cystine (DBC(650)).

The apoptotic Jurkat cell uptake of DBC shows not only that the xc- transporter is activated in cells undergoing oxidative stress (and in this case apoptosis), but also that the xc- transporter is promiscuous enough to allow this substrate (cystine) with amine appended green fluorophores (bodipyFL) into the cell. A labeled cystine derivative was synthesized with a red fluorophore (bodipy650) to further determine the promiscuity of the transporter. In a side-by-side comparison to the bodipyFL labeled cystine, DBC-650 did not appear to label apoptotic cells any more than normal cells, as shown in FIGS. 4A and 4B, indicating that some labels are not sufficient for maintaining xc- transporter substrate status. In this example, the bodipy-650 fluorophore and associated linker are larger than that of DBC (FIG. 4A), and therefore size represents one limitation of what groups are appended to the amines while retaining the ability to pass through the transporter.

EXAMPLE 4

From the previous example, it is important to keep the size of the label small. Smaller labeled cystine molecules serve as more appropriate substrates than larger cystine molecules such as DBC-650 and DBC. Therefore, a smaller fluorescent cystine molecule was synthesized, with the fluorescent label Bodipy at only one of the amines, MonoBodipyCystine (MBC). This molecule was created using commercially available cystine and BODIPY-FL succinimidyl ester (Invitrogen, D2184), purified by reverse phase- HPLC and analyzed by mass spectrometry to confirm the correct product. MBC has the structure shown below.

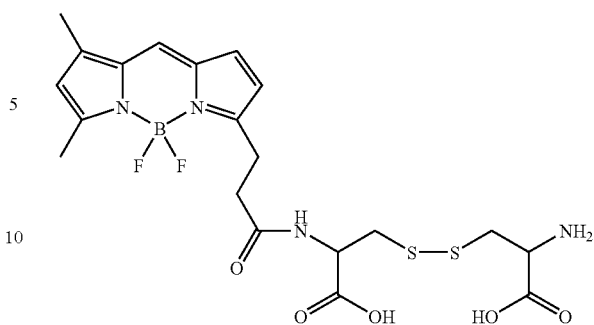

Figure 5C:
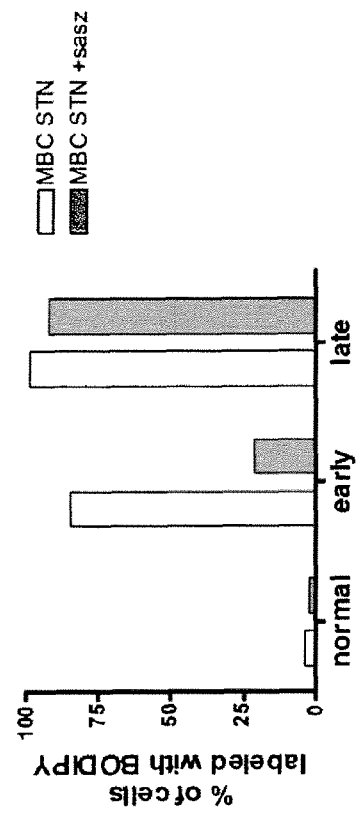
FIG. 5C is a bar chart showing the percentage of cells labeled greater than baseline MBC staining for normal, early apoptotic and late apoptotic cells (as determined by AnnexinV and PI staining).
Figure 5A:
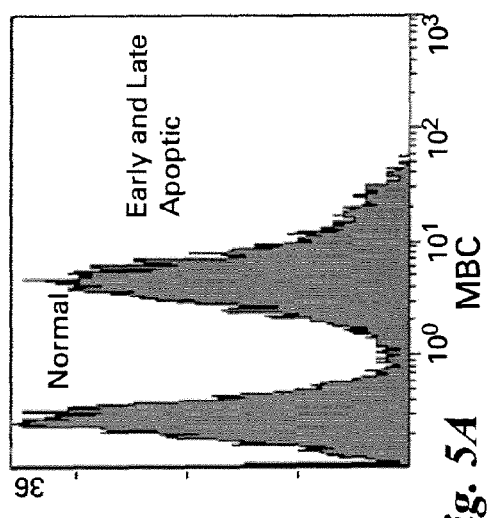
FIG. 5A is a graph showing that staurosporine induced cells have two subpopulations of cells, no MBC fluorescence representing normal cells and high MBC intensity representing early and late apoptotic cells.
Figure 5B:
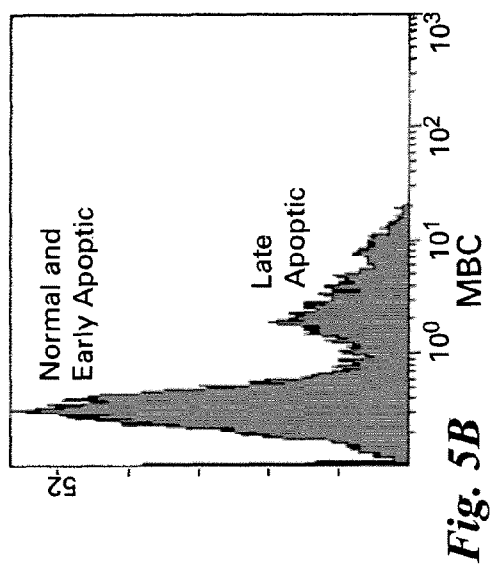
FIG. 5B is a graph showing that staurosporine induced that are exposed to the cystine/glutamate transporter inhibitor sulfasalazine (sasz) have a different result; a population of cells with intermediate MBC staining represents late apoptotic cells, while early apoptotic cells show no MBC fluorescence intensity.

Jurkat cells were incubated with 1 μM STN for 16-18 hours, stained with Annexin V-Cy5 and propidium iodide, and incubated with MBC for 30 minutes, without (FIG. 5A) and with (FIG. 5B) the addition of the cystine/glutamate inhibitor (sasz). In FIG. 5A, MBC labeling is visualized as a subpopulation of cells with a high intensity fluorescence shift, which corresponds well with both early and late apoptotic cells (FIG. 5C). No intermediate population was evident, suggesting that MBC labeled early apoptotic cells with greater intensity than DBC. In FIG. 5B, the addition of sulfasalazine results in fewer labeled cells and with less of a shift in fluorescence intensity. This population correlated well with late apoptotic cells and did not correlate well with early apoptotic cells (FIG. 5C). In this example, MBC is smaller than DBC (with only one label) and more closely resembles the natural transporter substrate cystine; resulting in an agent with improved performance for labeling early apoptotic cells. With MBC, there is less background uptake in normal cells, without sacrificing the magnitude of increase in fluorescence intensity for apoptotic cells, even though there is one less fluorophore per cystine molecule.

EXAMPLE 5

Agents that contain a reducible disulfide bond should be reduced inside of the intracellular compartment and therefore would not be a substrate for efflux by the cystine/glutamate transporter and would result in trapping the label inside the cells, to show this action, a DiBodipy Cystathionine (DBCystathionine) agent was formulated with the following structure.

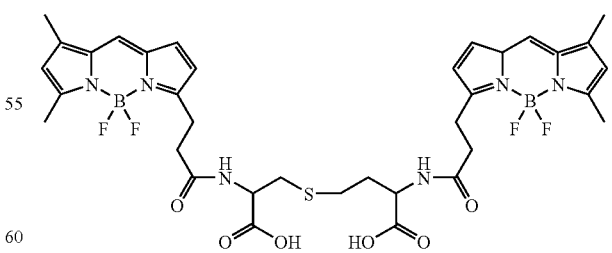

Also used as a negative control, was Bodipy-FL C5, which is available commercially from Invitrogen that has the following structure.

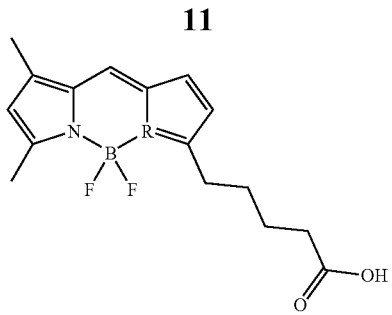

Figures 6A, 6B:
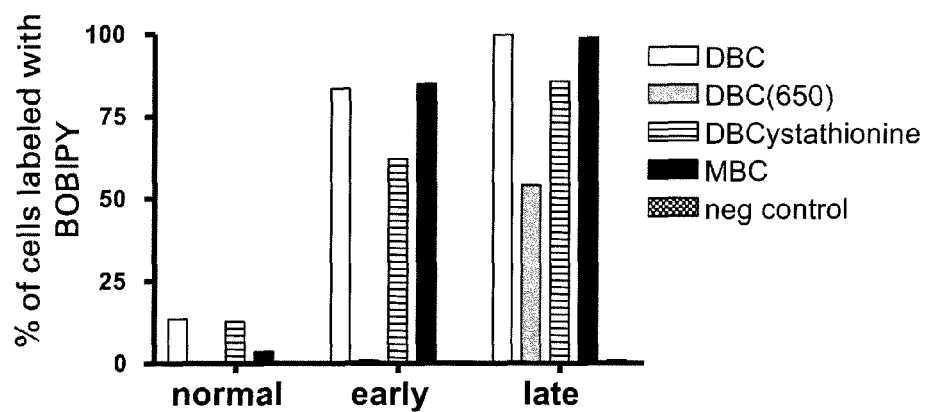
FIG. 6A is a bar chart showing the percentage of normal, early apoptotic and late apoptotic cells (as determined by Annexin V and PI staining) cells labeled with five different fluorescent agents, DBC, DBC(650), DiBodipyCystathionine(DBCystathionine), MBC and a negative control fluorescent molecule (Bodipy-FL C5).
FIG. 6B is a table showing the mean fold intensity shift for early apoptotic cells that are labeled with each of the five agents shown in FIG. 6A.

FIG. 6A shows a comparison of Bodipy staining of normal, early apoptotic and late apoptotic Jurkat cells with DBC, DBC(650), DBCystathionine, MBC and the negative control (Bodipy-FL C5). DBC, DBCystathionine, and MBC stain early apoptotic cells, DBC(650) only stains late apoptotic cells, and the negative control does not show any shift in fluorescence for apoptotic cells. From this data, DBC, DBCystathionine, and MBC are all equivalent labels for apoptotic cells. However, in FIG. 6B, the fold shift in fluorescence intensity of the early apoptotic cells is compared to normal cells for each agent. It is clear that MBC provides more intense staining than the other fluorescent agents used.

EXAMPLE 6

As evident from the previous examples, it is beneficial to have a single small label. Smaller labeled cystine molecules serve as more appropriate substrates than larger labeled cystine molecules such as DBC-650. Therefore, cystine molecules were synthesized with a single amine conjugated to [18F]aminoxy-fluorobenzadehyde (monoAO-[18F]-FBA-Cystine), and may be used for PET imaging applications. First the aminoxy-cystine precursor (MonoAO-cystine) was synthesized, with the following structure.

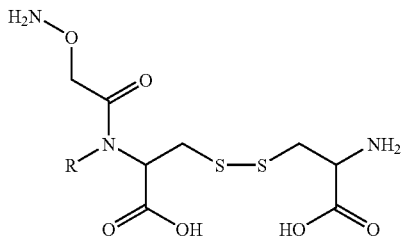

Generally, the monoAO-cystine was then conjugated to [18F]Fluorobenzaldehyde to yield monoAO-[18F]-FBA-Cystine with the following structure.

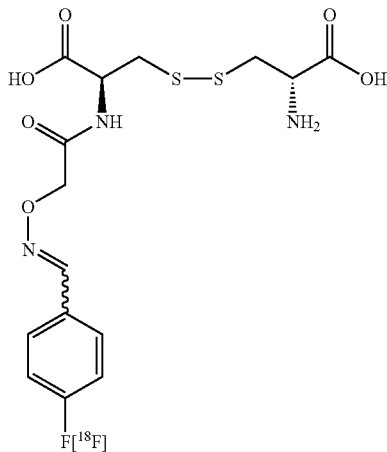

A more specific, non-limiting example of the method for synthesizing the monoAO-[18F]-FBA-Cystine is provided as follows.

All reactions were performed either under a nitrogen atmosphere or in a crimp-top sealed vial purged with nitrogen. Kryptofix 222 (Aldrich) and K2CO3 (EMD Science) were purchased and used as received. Optima™-grade acetonitrile was used as both HPLC and reaction solvents.

[18F]KF (40 mCi.mL−1 (1480 MBq.mL−1) in purified water) was obtained from either IBA Molecular (Albany, N.Y.) or PETNET Solutions (Albany. N.Y.) and used as received. The [18F]fluoride was first immobilized on a Chromafix 30-PS-HCO3 anion exchange cartridge (ABX, Radeberg, Germany), then eluted into a drydown vessel with a 1 mL, 4:1 mixture of acetonitrile:distilled deionized water (ddH$_2$O) containing Kryptofix K222 (376 g.mol−1, 8 mg, 2.13×10$^{-5}$ mol) and potassium carbonate (138.2 g.mol−1, 2.1 mg, 1.52×10$^{-5}$ mol). The solvent was removed under partial vacuum and a flow of nitrogen with gentle heating (~45° C.) (~15 min). The source vial and anion exchange cartridge were then washed with 0.5 mL of acetonitrile containing K222 (8 mg) and the reaction mixture again brought to dryness under partial vacuum and gentle heating (~10 min). The reaction vessel was repressurized with nitrogen and the azeotropic drydown repeated twice with an additional 0.5 mL of acetonitrile. 4-formyl-N,N,N-trimethylanilinium triflate (313.30 g.mol−1, 3.1 mg, 9.89×10$^{-6}$ mol) was dissolved in 0.35 mL of anhydrous DMSO (Acros) and added directly to the reaction vessel containing the [18F]KF.K222, K2CO3. The reaction mixture was heated to 90° C. for 15 min and immediately cooled and quenched with 3 mL of distilled, deionized H$_2$O (ddH$_2$O). This mixture was subsequently passed through a cation exchange cartridge (Waters SepPak Light Accell Plus CM), diluted to 10 mL with ddH2O, and loaded onto a reverse phase C18 SepPak (Waters SepPak Plus C18). The SepPak was flushed with 10 mL of ddH$_2$O then purged with 30 mL of air. [18F]4-fluorobenzaldehyde ([18F]FBA), was eluted in 1.0 mL of methanol.

Separately, a high recovery vial (2 mL, National Scientific) was charged with mono-aminoxy cystine (386.27 g.mol$^{-1}$, 2.7 mg, 6.99×10$^{-6}$ mol). The solid was suspended in 250 µL of ddH2O and 8 µL of trifluoroacetic acid. 500 µL of [18F] FBA in methanol (see above) was transferred to the reaction vial. The vessel was capped, crimped, placed in a heating block (activity at start of reaction 4.66 mCi/172 MBq) and maintained at 60° C. for 15 minutes; at which point a small aliquot (<5 µL) was removed for analytical HPLC analysis. 250 µL of ddH$_2$O with 0.1% TFA was used to dilute the solution to approx. 1000 µL, giving a final composition of 1:1 ddH$_2$O:MeOH in preparation for semi-preparative HPLC purification. [18F]FB-Cystine was isolated and purified by semi-preparative HPLC. The HPLC fraction containing the product (0.409 mCi/15.1 MBq) was diluted 5:1 with ddH$_2$O and subsequently immobilized on a tC18 Plus Sep Pak (Waters). The SepPak was flushed first with 5 mL of ddH$_2$O then 30 mL of air. [18F]FB-Cys (0.17 mCi, 6.3 MBq) was isolated in a minimal amount of DMSO by first eluting the void volume (approx. 0.5 mL) followed by collecting 250 to 300 µL of eluent in a separate flask. RP-HPLC analysis was performed on the isolated product in order to establish radiochemical and chemical purity. Typically, 10 µL of a 0.1 µCi/µL solution was injected for post formulation analysis. Isolated radiochemical yield was 3.6% (6.6% decay corrected from addition of [18F]FBA) and radiochemical purity of 96.8%.

Analytical HPLC conditions: Analysis performed on an HP Agilent 1100 with a G1311A QuatPump, G1313A autoinjector with 100 µL syringe and 2.0 mL seat capillary, Phenomenex Gemini C18 column (4.6 mm×150 mm), 5 µ, 100 Å (S/N 420477-10), G1316A column heater, G1315A DAD and Ramon Star—GABI gamma-detector. 95:5 ddH₂):CH₃CN with 0.05% TFA, Solvent B: CH₃CN with 0.05% TFA. Gradient elution: 0 min. 0% B, 1 min. 15% B, 10 min. 31% B, 10.5 min. 100% B, 13.5 min. 100% B, 14 min. 0% B, 17 min. 0% B. (TR~7.1 min)

Semipreparative HPLC conditions: Purification was performed on a Jasco LC with a DG-2080-54 4-line Degasser, an MX-2080-32 Dynamic Mixer and two PU-2086 Plus Prep pumps, an AS-2055 Plus Intelligent autoinjector with large volume injection kit installed, a Phenomenex 5μ. Luna C18 (2) 100 Å, 250×10 mm, 5μ, column with guard (S/N 295860-1, P/N 00G-4252-N0), an MD-2055 PDA and a Carroll & Ramsey Associates Model 105S Analogue Ratemeter attached to a solid-state SiPIN photodiode gamma detector. Gradient elution: 0 min. 0% B, 3 min. 20% B, 42 min. 70% B, 42.5 min. 100% B, 46 min. 100% B, 50 min. 0% B, Solvent A: ddH₂O:CH₃CN with 0.05% TFA, Solvent B: CH₃CN with 0.05% TFA. (TR ~14.7 min)

Figure 7:
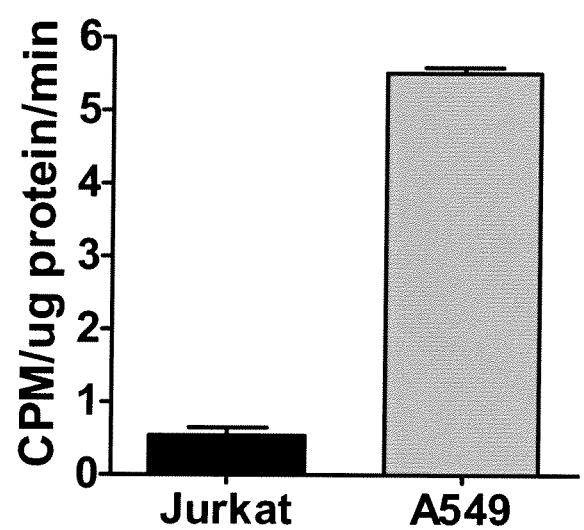
FIG. 7 is a bar graph showing the uptake of [18F]FB-monoAO-Cystine in Jurkat and A549 cells in culture.

The monoAO-[18F]-FBA-Cystine was used in an in vitro cell uptake assay, wherein monoAO-[18F]-FBA-Cystine was incubated with cultured cells for 30 minutes and washed twice with saline before lysing the cells with 1N NaOH and collection for analysis in a gamma counter. FIG. 7, shows the uptake of monoAO-[18F]-FBA-Cystine in two different cell lines, indicating differential basal expression and activity of the cystine/glutamate transporter in Jurkat and A549 cell lines.

Figure 8A:
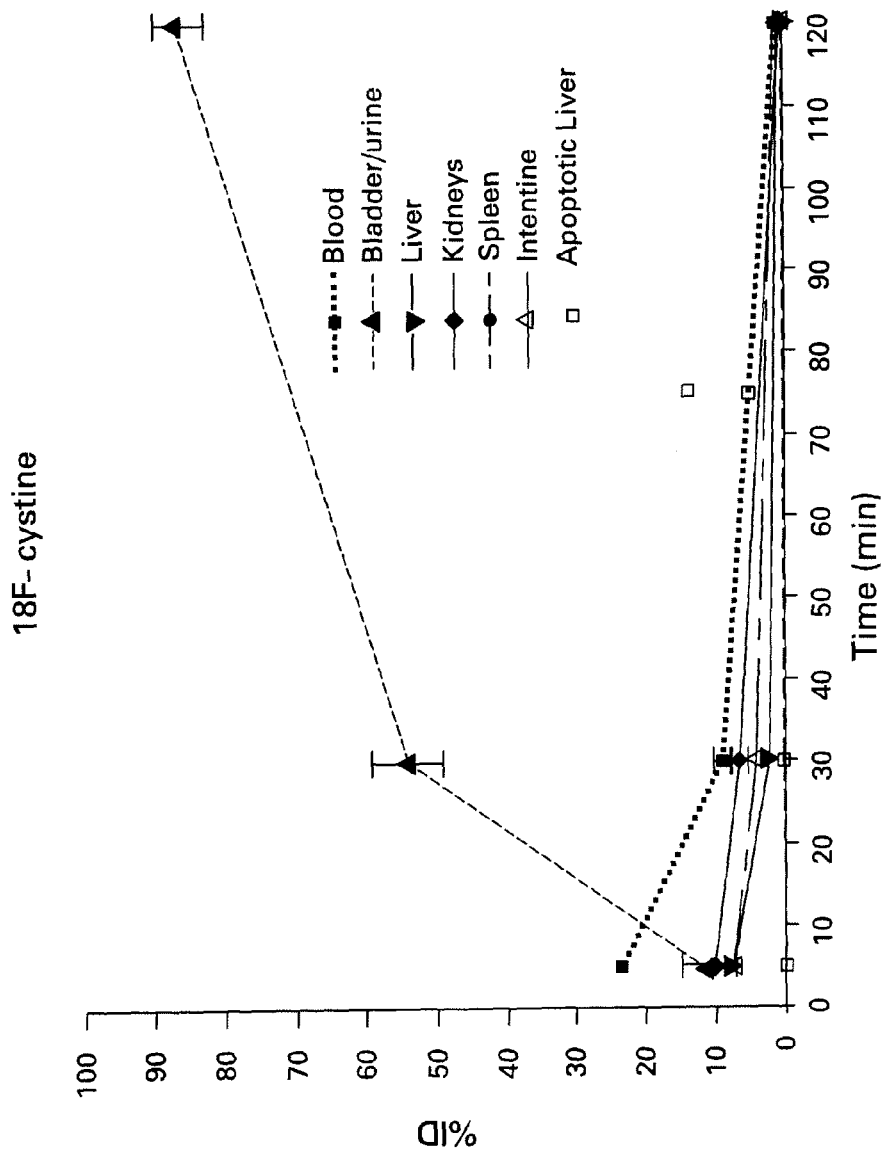
FIG. 8A is a graph showing the biodistribution results in naïve Balb-c mice in % ID/organ.
Figure 8B:
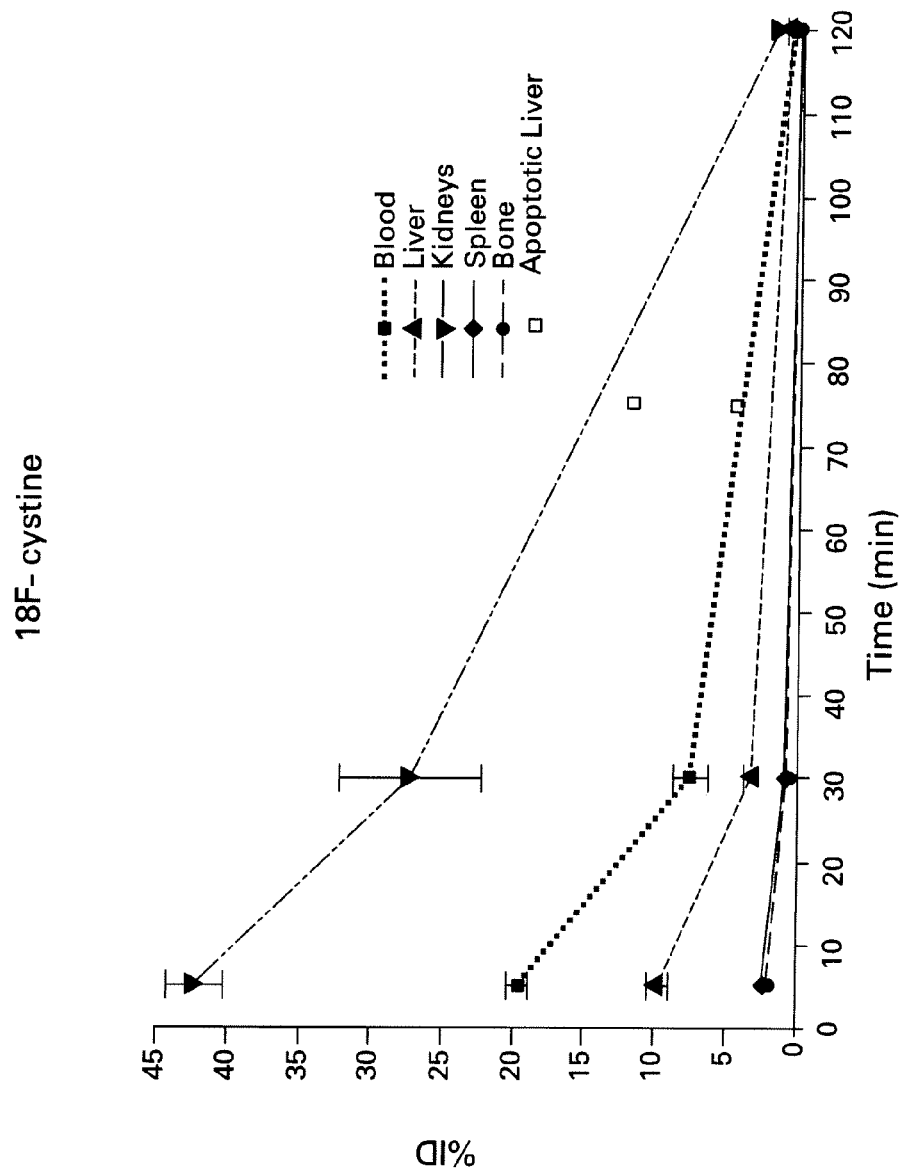
FIG. 8B is a graph showing the % ID/gram of the same data shown in FIG. 8A.

A pharmacokinetic profile of this molecule, which was formulated into 7% ethanol in saline, was established in normal mice and is shown in FIGS. 8A and 8B. The naïve Balb/c mice were injected ~15 uCi with 18F-cystine and time points were taken at 5, 30, 120 min post injection. FIG. 8A shows the biodistribution results in naïve Balb-c mice, % of injected dose (% ID). Clearance from the body is largely due to renal excretion as shown by the profile of the kidney, bladder and urine. FIG. 8B shows the % ID/gram of the same data shown in FIG. 8A. In two mice, apoptosis was induced with an injection of anti-Fas antibody two hours before injection of the radiotracer. Two animals were investigated that received anti-Fas antibody injections 2 hours prior to the mono AO-18F-FBA-Cystine injection to induce apoptosis in the liver. While the number of animals investigated thus far is low, both show liver uptake above the control animals.

Figures 8C, 8D:
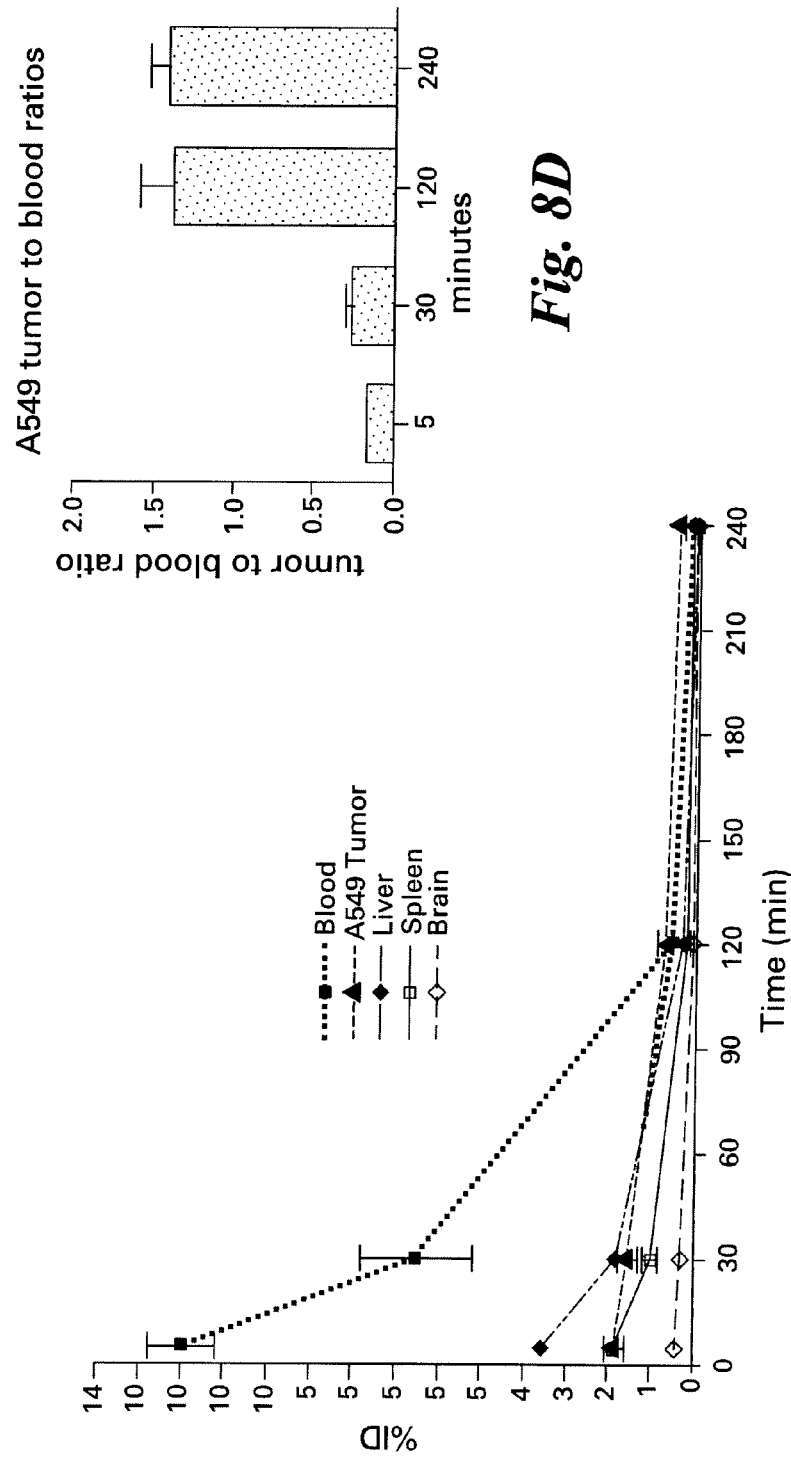
FIG. 8C is a graph showing biodistribution results in nude mice with A549 xenograft tumors in % ID/gram.
FIG. 8D shows tumor to blood ratios at each timepoint and is derived from the same data shown in 8C.

FIG. 8C shows a similar biodistribution results in % ID/gram from a study done in nude mice with A549 tumor xenografts. At 120 minute and 240 minute time points the radiotracer has cleared sufficiently to detect more % ID/gram in the tumor than in blood or other tissues (except kidney and bladder). Tumor to blood ratios are shown for each time point in FIG. 8D. These results suggest that radiolabeled cystine analogs can be used for the detection of cystine/glutamate transporter activity in vivo.

Figure 9:
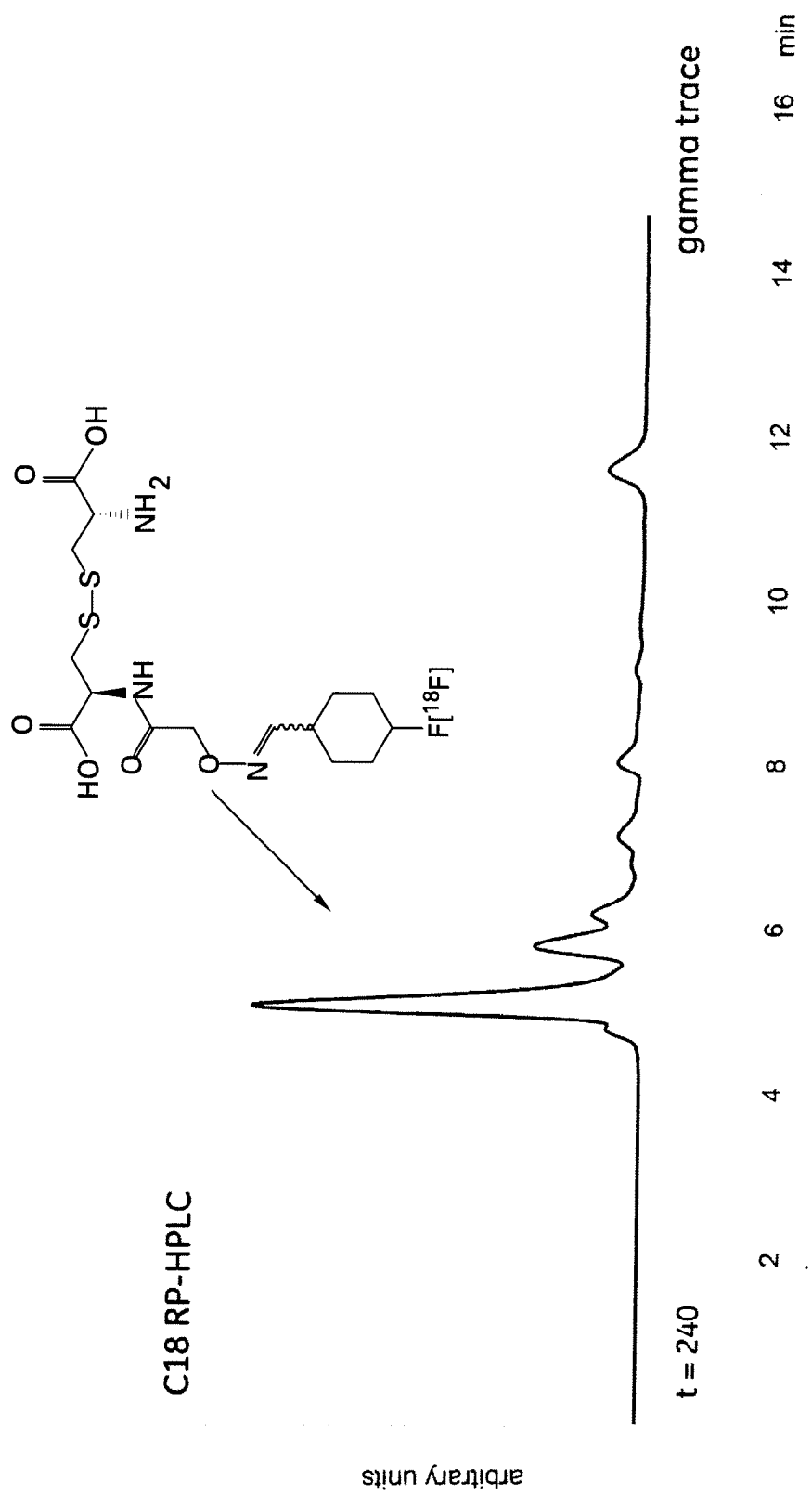
FIG. 9 is a graph showing the stability of the [18F]FB-monoAO-Cystine molecule over time.

FIG. 9 shows the stability of the [18F]FB-monoAO-Cystine molecule over time in saline. As shown, there was not any change in the gamma-trace profile over a 4-hour period.

Figure 10:
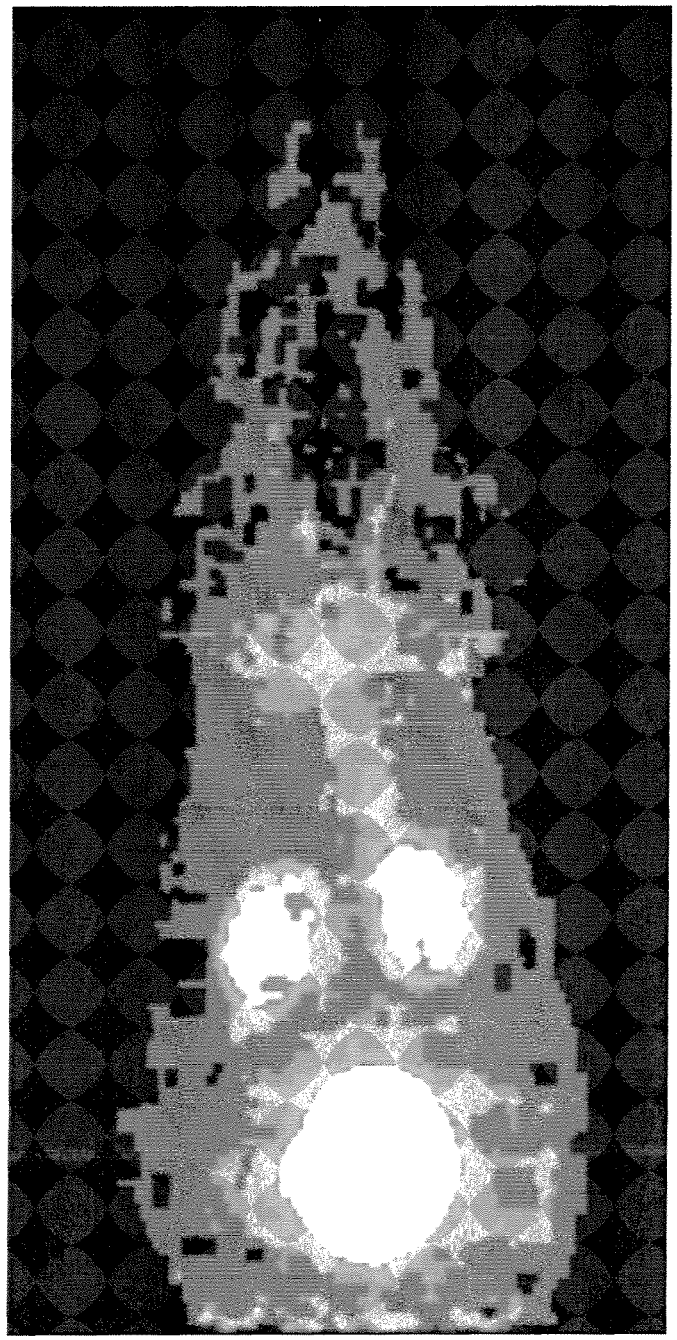
FIG. 10 is an image showing the 18F-AO-FB-Cystine in a PET image in a naïve mouse at 60 minutes post injection.

FIG. 10 shows the 18F-AO-FB-Cystine in a PET image in a naïve mouse at 60 minutes post injection, showing clearance primarily through the kidneys and bladder.

As another non-limiting example, the cystine may be labeled with 1-123 iodobenzaldehyde, which similar fluorobenzaldehyde, may be prepared by first adding [¹²³I]4-iodobenzaldehyde ([¹²³I]IBA) to a high recovery vial (2 mL, National Scientific) containing the AO-Cys, 2.5 mg). The reaction commences by dissolving the polypeptide in 0.5 mL of ddH₂O and adding 8 μL of trifluoroacetic acid followed by the addition of [¹²³I]IBA in 0.5 mL of methanol. The vessel is capped, crimped, placed in a heating block and maintained at 60° C. for 15 minutes; removing a small aliquot (<5 μL) for analytical HPLC analysis is done to assess the status of the reaction. [¹²³I]IB-Cystine is isolated and purified by semi-preparative HPLC. The HPLC fraction containing the product is further diluted (5:1) with ddH₂O and the product subsequently immobilized on a tC18 Plus Sep Pak (Waters). Flushing the SepPak first with 5 mL of ddH₂O then 30 mL of air gives the [¹²³I]IB-Cystine in a minimal amount of ethanol by first eluting the void volume (approx. 0.5 mL) followed by collecting 250 to 300 μL of eluent in a separate flask. RP-HPLC analysis is then performed on the isolated product to establish radiochemical and chemical purity.

Other examples include, but are not limited to: [¹⁸F]fluoroethyl-cystine or [¹⁸F]FE-cystine having the structure V:

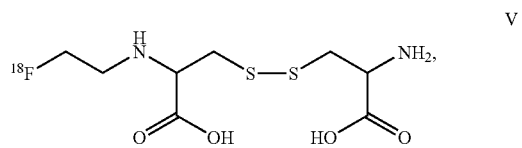

and [¹⁸F]fluoropropanamido-cystine or [¹⁸F]FP-cystine having the Structure VI:

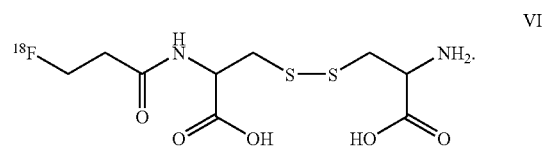 [SMILES: NC(CSSCC(NC(=O)CC[18F])C(=O)O)C(=O)O]

These agents that are taken up into cells via the cystine/glutamate antiporter (xc- transporter system) may be used to image cellular oxidative stress in vivo, including without limitation, the imaging of pathologies or conditions that include cellular oxidative stress. Imaging applications that would benefit from these agents include, but are not limited to, chemotherapy treatment monitoring, ischemia/stroke, inflammation, traumatic brain injury and organ transplant monitoring.

Radioisotope labels such as $^{123}$—I, $^{125}$—I, $^{131}$—I, $^{18}$—F, $^{11}$C, $^{62}$Cu, $^{64}$Cu, $^{67}$Cu, $^{67}$Ga and $^{68}$Ga may be particularly useful for in vivo PET or SPECT imaging as well as in vitro detection of cellular oxidative stress. While fluorescent labels, such as Bodipy fluorescent dyes, may be particularly suited for optical in vivo imaging and in vitro detection of cellular oxidative stress.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. An imaging agent mono-amine-labeled cystine compound having structure I,

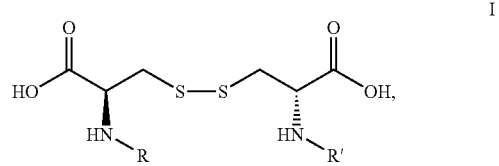

wherein R is a fluorescent or radioisotopic label conjugated to the amine and R' is H.

2. The imaging agent of claim 1, wherein the cystine compound has structure III:

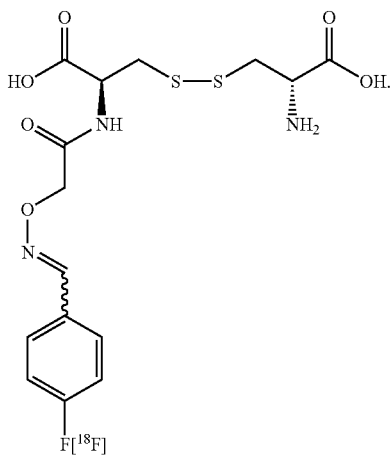

III

3. A method for detecting oxidative stress in cells comprising:
 introducing an imaging agent comprising a labeled cystine into a cystine/glutamate transporter of the cells;
 allowing the intracellular labeled cystine to be reduced into a labeled cysteine; and
 detecting the labeled cystine or the labeled cysteine in the cells in order to detect oxidative stress in the cells;
 wherein the labeled cystine is a mono-amine-labeled cystine compound having structure I,

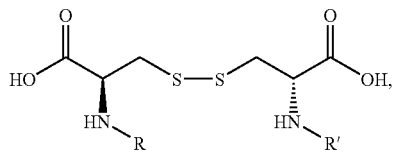

I wherein R is a fluorescent or radioisotopic label conjugated to the amine and R' is H.

4. The method of claim 3, wherein the cystine compound has structure III,

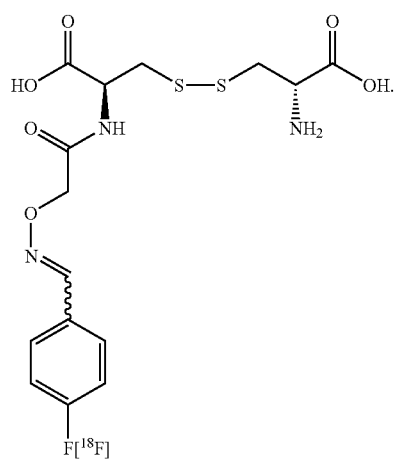

III

5. The method of claim 3, wherein the cystine compound is detected in apoptotic cells.

* * * * *